United States Patent [19]

Minderhoud et al.

[11] Patent Number: 4,587,008

[45] Date of Patent: May 6, 1986

[54] PROCESS COMPRISING REFORMING, SYNTHESIS, AND HYDROCRACKING

[75] Inventors: Johannes K. Minderhoud; Martin F. M. Post; Swan T. Sie; Ernst J. R. Sudhölter, all of Amsterdam, Netherlands

[73] Assignee: Shell Oil Company, Houston, Tex.

[21] Appl. No.: 666,527

[22] Filed: Oct. 30, 1984

[30] Foreign Application Priority Data

Nov. 15, 1983 [NL] Netherlands ............... 8303910

[51] Int. Cl.$^4$ ............... C07C 27/06; C10G 47/04
[52] U.S. Cl. ............... 208/109; 208/950; 518/714; 518/715
[58] Field of Search ............... 208/950, 109; 585/702, 585/715, 703, 704; 502/262, 236, 239; 518/714, 715

[56] References Cited

U.S. PATENT DOCUMENTS

| | | | |
|---|---|---|---|
| 1,979,841 | 11/1934 | Pier et al. ............... | 208/950 |
| 2,452,634 | 11/1948 | Clark ............... | 518/703 |
| 2,486,879 | 11/1949 | Rees et al. ............... | 518/703 |
| 2,609,382 | 9/1952 | Mayland ............... | 518/703 |
| 2,917,532 | 12/1959 | Watkins ............... | 518/704 |
| 3,169,107 | 2/1965 | Coonradt et al. ............... | 502/262 |
| 3,535,270 | 10/1970 | Mulaskey ............... | 502/262 |
| 4,044,064 | 8/1977 | Milstein et al. ............... | 208/950 |
| 4,279,830 | 7/1981 | Haag et al. ............... | 208/950 |
| 4,382,854 | 5/1983 | Wilson et al. ............... | 208/216 |
| 4,388,222 | 6/1983 | Wilson et al. ............... | 252/437 |
| 4,394,253 | 7/1983 | Van Nordstrand ............... | 208/251 |
| 4,443,561 | 4/1984 | Boelema et al. ............... | 518/704 |
| 4,471,145 | 9/1984 | Chu et al. ............... | 208/950 |
| 4,499,209 | 2/1985 | Hoek et al. ............... | 518/714 |
| 4,522,939 | 6/1985 | Minderhoud et al. ............... | 502/242 |

FOREIGN PATENT DOCUMENTS

| | | |
|---|---|---|
| 55-085458 | 6/1980 | Japan . |
| 2103647 | 2/1983 | United Kingdom ............... 518/702 |
| 2124963A | 2/1984 | United Kingdom . |

*Primary Examiner*—John Doll
*Assistant Examiner*—Lance Johnson
*Attorney, Agent, or Firm*—Kimbley L. Muller

[57] ABSTRACT

A two-step process is disclosed wherein $C_9^+$ hydrocarbons are prepared from $C_4^-$ hydrocarbons by steam reforming followed by Fischer-Tropsch synthesis over a special cobalt-containing catalyst. Yields of $C_9^+$ hydrocarbons are increased by recycling a gaseous fraction comprising unconverted $H_2$ and CO as well as $C_8^-$ hydrocarbon by-products and steam to the steam reformer.

16 Claims, No Drawings

PROCESS COMPRISING REFORMING, SYNTHESIS, AND HYDROCRACKING

BACKGROUND OF THE INVENTION

The invention relates to a process for the preparation of hydrocarbons starting from hydrocarbons having a smaller number of carbon atoms per molecule.

Hydrocarbons of at most four carbon atoms per molecule (hereinafter referred to as "$C_4^-$ hydrocarbons") can be converted into hydrocarbons having at least five carbon atoms per molecule (hereinafter referred to as "$C_5^+$ hydrocarbons") by a two-step process in which in the first step the $C_4^-$ hydrocarbons are converted by steam reforming into a mixture of carbon monoxide and hydrogen, which mixture is contacted in the second step at elevated temperature and pressure with a catalyst and thus converted into a mixture of hydrocarbons consisting substantially of $C_5^+$ hydrocarbons. The reaction which takes place in the second step of the process is known in the literature as the Fischer-Tropsch hydrocarbon synthesis. Catalysts often used for this reaction contain one or more metals from the iron group together with one or more promotors and a carrier material.

In order to increase the yield of $C_5^+$ hydrocarbons unconverted hydrogen and carbon monoxide present in the reaction product of the second step can be recycled. In order to increase the selectivity towards $C_5^+$ hydrocarbons the $C_4^-$ hydrocarbons formed as by-product can also be recycled. The two-step process using recycling can be carried out by dividing the reaction product of the second step into a gaseous fraction consisting substantially of $C_4^-$ hydrocarbons and unconverted hydrogen and carbon monoxide, and a liquid fraction consisting substantially of $C_5^+$ hydrocarbons and water formed during the hydrocarbon synthesis, and recycling the gaseous fraction to the first step.

Since the steam reforming of $C_4^-$ hydrocarbons leads to the formation of a $H_2/CO$ mixture having a $H_2/CO$ molar ratio higher than 2, whilst Fischer-Tropsch catalysts have a $H_2/CO$ consumption ratio of at most about 2, when carrying out the two-step process with the use of recycle, the excess hydrogen formed will have to be removed during the process in order to prevent $H_2$ build-up in the system. The quantity of hydrogen to be removed is determined, inter alia, by the $H/C$ atomic ratio of the feed for the first step and the CO-shift activity of the catalyst used in the second step. On the assumption of a stoichiometric conversion of the feed during the steam reforming, according to the equation

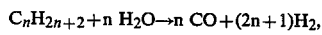
$$C_nH_{2n+2} + n\ H_2O \rightarrow n\ CO + (2n+1)H_2,$$

the synthesis gas obtained will have a higher $H_2/CO$ molar ratio according as the feed for the first step has a higher $H/C$ atomic ratio, and therefore more hydrogen will have to be removed during the process. For instance, starting from methane ($n=1$) as feed for the steam reforming, a synthesis gas can be obtained by the reaction given above which has a $H_2/CO$ molar ratio of $(2n+1)/n=3$. According as the catalyst used in the second step has higher CO-shift activity, a larger portion of the quantity of CO present in the synthesis gas will react with the water formed as by-product in the hydrocarbon synthesis according to the equation $CO+H_2O\rightarrow CO_2+H_2$, so that the $H_2/CO$ molar ratio will increase, and therefore more hydrogen will have to be removed in the process.

In order to keep the quantity of hydrogen to be removed as small as possible when carrying out the two-step process with use of recycle starting from a feed with a given $H/C$ atomic ratio, preference is given to the use in the second step of a catalyst with the highest possible $H_2/CO$ consumption ratio.

In the two-step process both the product of the first step and the product of the second step contain steam. The steam present in the product of the first step has found its way into that product at least partly on account of the fact that the steam reforming reaction is an incomplete reaction, so that even when a stoichiometric quantity of steam is used, a minor quantity thereof is found in the reaction product. For the protection of the catalyst the steam reforming is usually carried out in the presence of a considerable excess of steam. When excess steam is used in the steam reforming, this excess is found in the reaction product of the first step, together with the minor amount of steam mentioned hereinbefore. The steam present in the product of the second step has found its way into that product on account of the formation of steam as by-product in the hydrocarbon synthesis in the second step according to the equation $CO+2H_2\rightarrow-(CH_2)-+H_2O$.

As is seen from the above, when the steam reforming reaction and the hydrocarbon synthesis reaction proceed stoichiometrically, the quantity of steam used in the steam reforming will correspond substantially with the quantity of steam formed in the hydrocarbon synthesis. In order to keep the quantity of water which must be added to the process from outside as small as possible, it is preferred that both the water which has remained unconverted in the steam reforming and the water which has formed in the hydrocarbon synthesis are used in the first step of the process. The water which is present in the reaction product of the first step in the form of steam can be removed therefrom by condensation. The water which is present in the reaction product of the second step in the form of steam is found together with the $C_5^+$ hydrocarbons in the liquid fraction obtained in the gas/liquid separation carried out after the second step. Both water streams can be recycled to the first step.

Although the above-described two-step process, in which not only unconverted hydrogen and carbon monoxide and $C_4^-$ hydrocarbons formed as by-product are recycled to the first step, but also water from the reaction products both of the first and of the second step, offers the possibility of highly selectively preparing $C_5^+$ hydrocarbons, whilst the quantity of water which has to be fed to the process from outside is kept as small as possible, this process has a severe drawback. This drawback concerns the way in which the water is separated from the reaction products of the first and second step. As stated hereinbefore, this separation is carried out by condensation. This involves that steam whose pressure was originally at the process level be separated in the form of water, from which subsequently steam must be formed which must be re-pressurized to the process level before it can be introduced into the steam reforming. In view of the often big excess of steam used in the steam reforming and the considerable amount of steam formed in the hydrocarbon synthesis (owing to the development of the Fischer-Tropsch reaction the reaction product of the second step contains more water than hydrocarbons, expressed by weight), this procedure entails high cost when carried out on a technical scale.

Naturally it would be much more attractive to leave the steam which has remained unconverted during the steam reforming in the reaction product and not to separate it until after the second step, together with steam formed in the second step. By dividing the reaction product of the second step into a liquid fraction consisting substantially of relatively high-boiling hydrocarbons and a gaseous fraction consisting substantially of unconverted hydrogen and carbon monoxide, stream and relatively low boiling hydrocarbons, and recycling the gaseous fraction to the steam reforming, a steam recycle might be brought about without there being the need—in order to separate steam—of successive condensation, evaporation of the water and re-pressurizing of the steam. However, application of this process on a technical scale is to a considerable extent dependent on the influence which steam has on the behavior of the catalyst in the second step and the selectivity of this catalyst to the formation of relatively high-boiling hydrocarbons. As regards the latter item the following may be remarked. If in the two-step process one is prepared to accept separation of steam in the form of water, the division of the reaction product of the second step can be simply brought about by bringing the product to a room temperature, so that the hydrocarbons are divided into substantially $C_4^-$ hydrocarbons which are recycled to the first step on the one hand and $C_5^+$ hydrocarbons which constitute the end product of the process on the other hand. In such a procedure it is the $C_5^+$ selectivity of the catalyst in the second step in particular which plays an important role. For at a given activity fewer $C_4^-$ hydrocarbons will be formed according as the catalyst has a higher $C_5^+$ selectivity, and therefore a smaller recycle stream will be sufficient. However, if in the two-step process it is the object to separate the steam per se, the division of the reaction product of the second step should be carried out at an elevated temperature, notably at a temperature which lies above the dew point of water at the prevailing pressure. In actual practice this means that where the hydrocarbons are concerned, there will be a division into substantially hydrocarbons having at most eight carbon atoms per molecule (hereinafter referred to as "$C_8^-$ hydrocarbons")on the one hand and substantially hydrocarbons having at least nine carbon atoms per molecule (hereinafter referred to as "$C_9^+$ hydrocarbons") on the other hand. In such a procedure it is the $C_9^+$ selectivity of the catalyst in the second step in particular that plays an important role. It should be high.

In order to get a fair knowledge of the influence of steam on the performance of Fischer-Tropsch catalysts, an investigation was carried out in which these catalysts were used for the conversion of gas mixtures, some containing steam in addition to $H_2$ and CO, some not. It was found that the presence of steam in the $H_2$/CO mixture decreased the activity of these catalysts. As regards the $C_9^+$ selectivity the investigation yielded a surprising find. Contrary to other Fischer-Tropsch catalysts upon whose $C_9^+$ selectivity the presence of steam has no, or else an adverse, effect, it was found for a certain group of cobalt catalysts that the presence of steam led to a considerable increase in their $C_9^+$ selectivity. The Fischer-Tropsch catalysts displaying this surprising behavior comprise silica, alumina or silica-alumina as carrier material and cobalt together with zirconium, titanium and/or chromium as catalytically active metals, in such quantities that in the catalysts there are present 3-60 pbw cobalt and 0.1-100 pbw zirconium, titanium and/or chromium per 100 pbw carrier material. The catalysts are prepared by depositing the metals involved by kneading and/or impregnation on the carrier material. For further information on the preparation of these catalysts by kneading and/or impregnation reference is made to U.S. Pat. No. 4,499,209, issued Feb. 12, 1985 and which and is incorporated herein by reference.

When a cobalt catalyst belonging to the above-mentioned class is used for the conversion of a $H_2$/CO mixture containing no steam, it is seen that under the given reaction conditions this catalyst, in addition to a high stability and $C_9^+$ selectivity, has a very high activity. If the same catalyst is used under the same reaction conditions for converting a gas mixture containing steam in addition to $H_2$ and CO, a decrease in activity is seen, as remarked earlier, which decrease is smaller, by the way, than seen for other Fischer-Tropsch catalysts when an equal amount of steam is added to the gas mixture to be converted. However, for the cobalt catalysts there is seen beside the decrease in activity a considerable rise in $C_9^+$ selectivity. In view of the very high degree of activity of the present cobalt catalysts some loss of activity in exchange for a considerable increase in $C_9^+$ selectivity is quite acceptable for an operation on a technical scale. These special features combined with a very high $H_2$/CO consumption ratio of about 2 render the cobalt catalysts eminently suitable for use in the second step of the afore-mentioned two-step process for the preparation of $C_9^+$ hydrocarbons which is carried out with recycle of a steam-containing gaseous fraction.

SUMMARY OF THE INVENTION

The present patent application therefore relates to a two-step process for the preparation of $C_9^+$ hydrocarbons from $C_4^-$ hydrocarbons, in which $C_4^-$ hydrocarbons are converted in the first step by steam reforming into a mixture of carbon monoxide and hydrogen, which mixture is subsequently converted in the second step into a mixture of hydrocarbons consisting substantially of $C_9^+$ hydrocarbons, by contacting it at elevated temperature and pressure with a catalyst comprising 3-60 pbw cobalt and 0.1-100 pbw of at least one other metal chosen from the group formed by zirconium, titanium and chromium per 100 pbw silica, alumina or silica-alumina, which catalyst has been prepared by kneading and/or impregnation, in which the reaction product of the second step is divided into a gaseous fraction consisting substantially of unconverted hydrogen and carbon monoxide, $C_8^-$ hydrocarbons formed as by-product and steam which has remained unconverted in the steam reforming as well as steam which was formed as by-product in the second step, and a liquid fraction consisting substantially of $C_9^+$ hydrocarbons, in which the gaseous fraction is recycled to the first step, and in which the excess of hydrogen formed is separated off during the process.

DETAILED DESCRIPTION OF THE INVENTION

In the process according to the invention the starting material is a feed consisting substantially of one or more $C_4^-$ hydrocarbons. Examples of $C_4^-$ hydrocarbons which may be present in the feed individually or in admixture are methane, ethane, propane, butane and isobutane. By preference the process is carried out with a feed in which the $C_4^-$ hydrocarbons consist substantially of methane. Special preference is given to natural gas as feed.

In the process according to the invention steam reforming is used in the first step to convert the $C_4^-$ hydrocarbons into a mixture of carbon monoxide and hydrogen. The steam reforming is usually carried out by contacting the hydrocarbons to be converted, together with steam, at a temperature of 500°-1200° C., a pressure 2-40 bar and a steam/hydrocarbon ratio of 1-10 g mol $H_2O$/g atom C with a catalyst containing one or more metals from the iron group supported on a carrier. The steam reforming is preferably carried out at a temperature of 700°-1000° C., a pressure of 2-25 bar and a steam/hydrocarbon ratio of 1.5-5 g mol $H_2O$/g atom C and by using a nickel-containing catalyst. In order to prevent deposition of coke on the catalyst and also to remove coke already deposited from the catalyst by conversion into CO, it is preferred to use a catalyst containing an alkali metal, in particular potassium. Moreover, in order to avoid sintering of the catalyst, it is preferred to use a catalyst containing an alkaline earth metal, in particular calcium. If the $C_4^-$ hydrocarbons in the feed consist completely or to a considerable extent of hydrocarbons containing two or more carbon atoms per molecule, it is preferred to use a catalyst having cracking activity. The catalyst can be invested with cracking activity by the use of a silica-alumina as carrier material.

The $C_8^-$ hydrocarbons which in the process according to the invention are recycled to the first step have been formed substantially as by-products in the second step. In addition minor quantities of $C_4^-$ hydrocarbons may find their way into the reaction product because a small portion of the $C_4^-$ hydrocarbons used as feed remains unconverted or is only cracked to form $C_4^-$ hydrocarbons with a smaller number of carbon atoms.

In the process of the invention it is preferred to use in the second step the cobalt catalysts which form the subject matter of Netherlands patent application No. 8301922. These are catalysts which satisfy the relation $$(3+4R) > L/S > (0.3+0.4R),$$

wherein

L = the total quantity of cobalt present on the catalyst, expressed as mg Co/ml catalyst,
S = the surface area of the catalyst, expressed as $m^2$/ml catalyst, and
R = the weight ratio of the quantity of cobalt deposited on the catalyst by kneading to the total quantity of cobalt present on the catalyst.

The preparation of the cobalt catalysts which are used in the second step of the process of the invention is preferably carried out according to one of the three procedures mentioned hereinafter:

(a) first cobalt is deposited in one or more steps by impregnation and subsequently the other metal is deposited in one or more steps, also by impregnation, (b) first the other metal is deposited in one or more steps by impregnation and subsequently the cobalt is deposited in one or more steps, also by impregnation, and (c) first cobalt is deposited in one or more steps by kneading and subsequently the other metal is deposited in one or more steps by impregnation.

In the process according to the invention preference is given to the use in the second step of cobalt catalysts containing 15-50 pbw cobalt per 100 pbw carrier. The preferred quantity of other metal present in the cobalt catalysts depends on the way in which this metal has been deposited. In the case of catalysts where first cobalt has been deposited on the carrier, followed by the other metal, preference is given to catalysts containing 0.1-5 pbw other metal per 100 pbw carrier. In the case of catalyst where first the other metal has been deposited on the carrier, followed by the cobalt, preference is given to catalysts containing 5-40 pbw of the other metal per 100 pbw carrier. Preference is given to zirconium as other metal and to silica as carrier material. In order to be suitable for use the cobalt catalyst should first be reduced. This reduction may suitably be carried out by contacting the catalyst at a temperature between 200° and 350° C. with a hydrogen-containing gas.

In the process according to the invention the excess hydrogen formed should be removed from the reaction product. For the removal of hydrogen from the reaction product the known techniques for removing hydrogen from gas mixtures are eligible. For instance, in the present process the removal of part of the hydrogen from the reaction product can very suitably be carried out by using what is called pressure swing adsorption. This involves contacting the gas mixture from which hyrogen is to be removed under pressure with a solid adsorbent, such as a molecular sieve, active carbon or a mixture thereof, leading to selective adsorption of the components present in the gas mixture beside hydrogen. The components adsorbed from the gas mixture by the adsorbent can be desorbed by reduction of pressure and re-pressurized to the original pressure level by compression. In the present process the removal of part of the hydrogen from the reaction product by using pressure swing adsorption can very suitably be carried out by applying this technique to a partial stream of the reaction product and, after hydrogen removal and compression, feeding this partial stream back into the main stream. In the present process the removal of part of the hydrogen from the reaction product can very suitably be carried out by membrane separation as well. To this end the reaction product or part thereof is passed along a membrane, often consisting substantially of a polymer material which has the property of being more permeable to hydrogen than to the other components of the reaction mixture. If desired, the reduction of the hydrogen content of the reaction product by using membrane separation can be carried out in more than one step. The separation of the excess hydrogen formed from the reaction product can be applied at choice, either to the reaction product of the first step, or to the gaseous fraction obtained after the gas/liquid separation following the second step. Since at the present state of the art the removal of hydrogen from gas mixtures by using membrane separation or pressure swing adsorption is still problematic when the gas mixtures concerned contain steam, in the present process the removal of hydrogen is preferably applied to a partial stream from which steam has been removed in advance by condensation. As remarked hereinafter, at stoichiometric development of the steam reforming reaction and the hydrocarbon synthesis reaction, the quantity of steam consumed in the steam reforming will correspond substantially with the quantity of steam formed in the hydrocarbon synthesis. This means that the process of the invention, in which steam is recycled, could in principle be carried out with only a minor quantity of steam—needed to compensate for occurring losses of steam—having to be fed into the process from outside. However, if for removing the excess of hydrogen formed use is made of a partial stream from which steam is first removed by condensation—as described hereinbefore—, it should be taken into account that beside the afore-mentioned minor quantity of steam, an additional quantity of steam, corresponding with that removed from the partial stream by condensation, will have to be fed into the process. In comparison with the conventional process, in which there is no steam recycle, considerable cost savings will be achieved even when only part of the steam is recycled according to the present invention.

The cobalt catalysts used in the second step, in addition to the afore-mentioned surprising increase in $C_9^+$ selectivity in the presence of steam, display the special property of yielding a product which contains only very minor quantities of olefins and oxygen-containing organic compounds and whose organic part consists virtually completely of unbranched paraffins, a considerable percentage of which boils above the middle distillate range. In this patent application middle distillates are taken to be hydrocarbon mixtures whose boiling range corresponds substantially with that of the kerosine and gas oil fractions obtained in the conventional atmospheric distillation of crude mineral oil. The middle distillate range lies substantially between about 150° and 360° C., the fractions boiling between about 200° and 360° C. usually being referred to as gas oils. On account of the high normal paraffins/isoparaffins ratio and the low content of olefins and oxygen-containing organic compounds of the product prepared over the cobalt catalysts, the gas oil present therein has a very high cetane number. It has been found that by hydrocracking in the presence of a catalyst containing one or more noble metals of Group VIII supported on a carrier the high-boiling part of said product can be converted in high yield into middle distillate. As feed for the hydrocracking at least the part of the product is chosen whose initial boiling point lies above the final boiling point of the heaviest middle distillate desired as end product. The hydrocracking, which is characterized by a very low hydrogen consumption, yields a product in which, owing to the high normal paraffins/isoparaffins ratio, the gas oil has a very high cetane number. Although in the preparation of middle distillates from the product obtained over the cobalt catalyst the part of the product whose initial boiling point lies above the final boiling point of the heaviest middle distillate desired as end product will do as feed for the hydrocracking, it is preferred to use for this purpose the total $C_9^+$ fraction of the product prepared over the cobalt catalyst, since it has been found that the catalytic hydrotreatment leads to enhanced quality of the kerosine and gas oil fractions present therein.

The hydrocracking catalyst used by preference is a catalyst containing 0.1–2% w and in particular 0.2–1% w of one or more noble metals from Group VIII supported on a carrier. Preference is given to catalysts comprising platinum or palladium as Group VIII noble metal and silica-alumina as carrier. The hydrocracking in which the feed, together with added hydrogen, is passed over the noble metal catalyst is preferably carried out at a temperature of 200°–400° C. and in particular of 250°–350° C. and a pressure of 5–100 bar and in particular of 10–75 bar.

The invention is now illustrated with the aid of the following example.

EXAMPLE

This example relates to the preparation of $C_9^+$ hydrocarbons, starting from a natural gas substantially consisting of methane. The preparation was carried out by successively subjecting the natural gas, together with a recycle stream, in the first step to steam reforming, dividing the reaction product into a partial stream and a main stream in a 1:3 volume ratio, removing steam from the partial stream by cooling and hydrogen by applying pressure swing adsorption using a molecular sieve, mixing the partial stream freed of steam and hydrogen into the main stream, subjecting the mixture in a second step to hydrocarbon synthesis, dividing the reaction product $C_9^+$ hydrocarbons and a gaseous fraction comprising $C_8^-$ hydrocarbons, steam and unconverted hydrogen and carbon monoxide, and recycling the gaseous fraction to the first step. Further information on the conditions used for the preparation and the results obtained is given hereinafter.

STEAM REFORMING

The steam reforming was carried out at a temperature of 850° C. and a pressure of 22 bar and by using a steam/hydrocarbon ratio of 2.51 g mol $H_2O$/g mol $CH_4$ present in the fresh feed. The catalyst used was a Ni/Ca/K/$Al_2O_3$ composition containing 13 pbw nickel, 12 pbw calcium and 0.2 pbw potassium per 100 pbw alumina.

HYDROCARBON SYNTHESIS

The hydrocarbon synthesis was carried out at a temperature of 220° C., a pressure of 20 bar and a space velocity of 1100 Nl($H_2+CO$).$l^{-1}$.$h^{-1}$ and by using a Co/Zr/$SiO_2$ catalyst which had previously been subjected to reduction at 250° C. in a hydrogen-containing gas. The catalyst, which contained 25 pbw cobalt and 18 pbw zirconium per 100 pbw silica, had been prepared by three-step impregnation of a silica carrier with a solution of zirconium tetra-n-propoxide in a mixture of n-propanol and benzene, followed by single-step impregnation of the zirconium-loaded carrier with a solution of cobalt nitrate in water. In each of the impregnation steps there was used a quantity of solution whose volume corresponded substantially with the pore volume of the carrier. After each impregnation step the material was dried and then calcined at 500° C. The catalyst's L was 97 mg/ml and its S was 100 m²/ml and therefore the L/S was 0.97 mg/m².

The synthesis gas used as feed in the second step had a $H_2/CO$ molar ratio of 2.1 and contained 25% v steam (calculated on $H_2+CO+H_2O$). In the second step the synthesis gas conversion achieved was 90%. The $C_9^+$ selectivity, calculated on $C_1^+$ was 76%.

What is claimed is:

1. A process for the preparation of $C_9^+$ hydrocarbons from $C_4^-$ hydrocarbons present in a feed stream and $C_8^-$ hydrocarbons present in a recycle stream which comprises: (1) passing $C_4^-$ hydrocarbons as a feed stream and $C_8^-$ hydrocarbons as a recycle steam to a steam reforming zone to steam reform said hydrocarbons into a mixture of carbon monoxide and hydrogen at a temperature of from about 700° C. to 1000° C. and a pressure of from about 2 to about 25 bars in the presence of a steam reforming catalyst comprising an iron-group metal catalyst and, (2) passing at least a portion of said mixture of carbon monoxide and hydrogen from said steam reforming zone to a synthesis zone at an elevated temperature of about 125° to 350° C. and a pressure of from about 5-100 bar in contact with a catalyst comprising 3-60 pbw cobalt and 0.1 to 100 pbw of at least a second metal selected from the group consisting of zirconium, titanium and chromium all per 100 pbw of a support selected from the group consisting of silica, alumina and combinations of silica and alumina, which catalyst has been prepared by kneading or kneading and impregnating in accordance with:

$$(3+4R) > L/S > (0.3+0.4R),$$

wherein
- $L$ = the total quantity of cobalt present on the catalyst, expressed as mg Co/ml catalyst;
- $S$ = the surface area of the catalyst, expressed as $m^2$/ml catalyst; and
- $R$ = the weight ratio of the quantity of cobalt deposited on said support by kneading to the total quantity of cobalt present on the catalyst;

to form a product of a mixture of $C_9^+$ hydrocarbons, unconverted hydrogen, carbon monoxide, steam and a mixture of $C_8^-$ hydrocarbons, all of which is withdrawn and separated into (1) a liquid product stream comprising said $C_9^+$ hydrocarbons and (2) a gaseous stream comprising said unconverted hydrogen, carbon monoxide, steam and $C_8^-$ hydrocarbons and recycling at least a portion of said gaseous stream as said recycle stream said carbon monoxide, stream, $C_8^-$ hydrocarbons and at least a portion of said unconverted hydrogen in the gaseous phase as said recycle stream.

2. The process as claimed in claim 1, characterized in that said $C_4^-$ hydrocarbons feed is methane.

3. The process as claimed in claim 1, characterized in that said $C_4^-$ feed comprises natural gas.

4. The process as claimed in claim 1, characterized in that the reforming is carried out at a steam/hydrocarbon ratio of 1.5-5 mol $H_2O$/g atom C and that said iron-group metal catalyst is a nickel-containing catalyst.

5. The process as claimed in claim 1, characterized in that in the synthesis step said catalyst contains per 100 pbw support 15-50 pbw cobalt and 0.1-5 pbw of a second metal selected from the group consisting of zirconium, titanium and chromium if during the catalyst preparation cobalt was deposited first and the second metal next, or 5-40 pbw of the second metal if in the preparation the second metal was deposited first and cobalt next.

6. The process as claimed in claim 5, characterized in that zirconium is selected from the group consisting of zirconium, titanium and chromium and silica is selected from the group consisting of silica, alumina and silica-alumina.

7. The process as claimed in claim 1, characterized in that the second step is carried out at a temperature of 175°-275° C. and a pressure of 10-75 bar.

8. The process as claimed in claim 7, characterized in that at least a portion of said hydrogen is removed from said gaseous stream derived as a portion of said second step by membrane separation or by pressure swing adsorption.

9. The process as claimed in claim 8, characterized in that at least a portion of said hydrogen remains in said gaseous fraction obtained after gas/liquid separation following the second step and is recycled to step 1.

10. The process as claimed in claim 8, characterized in that during removal of at least a portion of said hydrogen, the gaseous stream is divided into a partial stream and a main stream, wherein steam is removed from the partial stream and then hydrogen is removed from the partial stream, and that the remaining partial stream, freed of steam and hydrogen, is mixed into the main stream.

11. The process of claim 1 wherein at least a portion of said liquid $C_9^+$ hydrocarbon product derived from the second step is subjected in a third process step to hydrocracking by contacting said $C_9^+$ hydrocarbon at elevated temperature and pressure with a catalyst comprising one or more noble metals from Group VIII of the Periodic Table supported on a carrier.

12. The process as claimed in claim 11, characterized in that said third hydrocracking step is performed in the presence of a catalyst containing 0.1-2% w of one or more noble metals from Group VIII of the Periodic Table.

13. The process as claimed in claim 12, characterized in that said third hydrocracking step is performed in the presence of a catalyst containing 0.2-1% w of one or more noble metals from Group VIII of the Periodic Table.

14. The process as claimed in claim 13, characterized in that said third hydrocracking step is performed in the presence of a catalyst containing platinum or palladium as noble metal from Group VIII of the Periodic Table deposited on silica-alumina as a carrier for said metals.

15. The process as claimed in claim 11, characterized in that said third hydrocracking step is performed at a temperature of 200°-400° C. and a pressure of 5-100 bar.

16. The process as claimed in claim 15, characterized in that said third hydrocracking step is performed at a temperature of 250°-350° C. and a pressure of 10-75 bar.

* * * * *